United States Patent [19]
Wille, Jr.

[11] Patent Number: 5,912,175
[45] Date of Patent: Jun. 15, 1999

[54] PROCESS AND MEDIA FOR THE GROWTH OF HUMAN CORNEA AND GINGIVA

[75] Inventor: John J. Wille, Jr., Trenton, N.J.

[73] Assignee: Hy-Gene, Inc., Ventura, Calif.

[21] Appl. No.: 09/133,386

[22] Filed: Aug. 13, 1998

Related U.S. Application Data

[63] Continuation of application No. 08/893,195, Jul. 15, 1997, Pat. No. 5,834,312, which is a continuation-in-part of application No. 08/500,744, Jul. 11, 1995, Pat. No. 5,686,307, which is a continuation of application No. 08/318,221, Oct. 5, 1994, abandoned, which is a continuation of application No. 08/184,905, Jan. 21, 1994, abandoned, which is a continuation of application No. 08/063,247, May 18, 1993, abandoned, which is a division of application No. 07/471,976, Jan. 29, 1990, Pat. No. 5,292,655.

[51] Int. Cl.$^6$ ....................................................... C12N 5/00
[52] U.S. Cl. ........................... 435/405; 435/325; 435/383; 435/384; 435/404
[58] Field of Search .................................. 435/405, 325, 435/383, 384, 404

*Primary Examiner*—Leon B. Lankford, Jr.
*Attorney, Agent, or Firm*—Donald O. Nickey; Standley & Gilcrest

[57] ABSTRACT

Media and methods are disclosed for the in vitro formation of a histologically complete human epithelium. The media are serum-free, companion cell or feeder layer free and organotypic, matrix free solutions for the isolation and cultivation of clonally competent basal epithelial cells. The media and methods of the invention are useful in the production of epithelial tissues such as epidermis, cornea, gingiva and ureter.

2 Claims, No Drawings

PROCESS AND MEDIA FOR THE GROWTH OF HUMAN CORNEA AND GINGIVA

RELATED APPLICATIONS

This application is a continuation of U.S. Ser. No. 08/893,195, filed Jul. 15, 1997, now U.S. Pat. No. 5,834,312; which is a continuation-in-part of U.S. Ser. No. 08/500,744, filed Jul. 11, 1995, now U.S. Pat. No. 5,686,307 issued Nov. 11, 1997, entitled SERUM-FREE MEDIUM FOR USE IN THE FORMATION OF A HISTOLOGICALLY COMPLETE LIVING HUMAN SKIN SUBSTITUTE; which is a continuation of U.S. Ser. No. 08/318,221, filed Oct. 5, 1994, now abandoned; which is a continuation of U.S. Ser. No. 08/184,905, filed Jan. 21, 1994, now abandoned; which is a continuation of Ser. No. 08/063,247, filed May 18, 1993, now abandoned; which is a divisional of U.S. Ser. No. 07/471,976, filed Jan. 29, 1990, now U.S. Pat. No. 5,292,655. U.S. Pat. Nos. 5,292,655 and 5,686,307 and 5,834,312 are incorporated herein by reference.

TECHNICAL FIELD OF THE INVENTION

The field of the invention is in biology and more specifically in the subspecialty of cell biology. The invention relates to a process and cell culture media for the growth of human epithelia, such as gingival epithelium, ureteral epithelium and corneal epithelium.

BACKGROUND OF THE INVENTION

The epithelium is the membranous cellular tissue that covers the surface or lines a tube or cavity of an animal body. The epithelium serves to enclose and protect the other parts of the body and may produce secretions and excretions and may be associated with assimilation as seen in the gastrointestinal tract. The epithelium is one of the four primary tissues of the body, which constitutes the epidermis and the lining of respiratory, digestive and genitourinary passages. The cornea, which is the transparent part of the coat of the eyeball that covers the iris and pupil and admits light to the interior, is also a tissue that is made of epithelial cells.

The functions of epithelia are varied and include: (1) protective function, by completely covering the external surface (including the gastrointestinal surface, the surface of the whole pulmonary tree including the alveoli and the eye); (2) secretory function, by secreting fluids and chemical substances necessary for digestion, lubrication, protection, excretion of waste products, reproduction and the regulation of metabolic processes of the body; (3) absorptive function, by absorbing nutritive substances and preserving water and salts of the body; (4) sensory function, by constituting important parts of sense organs, especially of smell and taste; and (5) lubricating function, by lining all of the internal cavities of the body, including the peritoneum, pleura, pericardium and the tuncia vaginalis of the testis.

The growth of human epithelial cells without the use of companion-cells, feeder layers, serum components or organotypic substrates is the advancement in the state of the art that is this invention. Traditionally, tissue culture of normal epithelial cells has been attempted in a variety of commercially available media designed for the growth of less fastidious types of cells, i.e., malignant cells transformed in vitro from cell lines derived from human or non-human tissues, cell lines developed from human or non-human tumors, or cell lines developed for human or non-human embryonic mesenchymal cell types. In contrast, the culture of normal human epithelial stem cells has presented many difficulties not the least of which is the inexorable tendency for these cells to undergo uncontrolled, irreversible, terminal differentiation with the consequent loss of cell division capacity.

A significant development made by Tsao et al. is the formulation of a nutrient medium supplemented with specified growth factors and hormones allowed for the growth of human epidermal cells. See Tsao, M. C. et al., *J Cellular Physiol.* 110:219–229 (1982). The Tsao medium has been designated MCDB 152. Further refinements of this medium lead to the development of a medium known as MCDB 153. See Boyce, S. T. and Ham, R. G., *J. Invest. Dermatol.* 81:33–40 (1983). The use of these media permitted a more accurate characterization of the necessary growth factors, hormones and $Ca^{2+}$ requirements for retention of high cloning efficiency which is necessary to maintain proper genetic programming for continued subculture of pluripotent basal epidermal stem cells. See Wille, J. J. et al., *J Cellular Physiol.* 121:31–44(1984).

The use of serum in cell culture medium provides a complex mixture of growth factors and differentiation-inducing factors. See Pittelkow, M. R. et al., *J. Invest, Dermatol.* 86:410–417 (1986). Pittelkow et al. reported that serum, known to contain fibroblastic cell growth factors, e.g., platelet-derived growth factor, was an inhibitor of basal epidermal cell growth. Further, the differentiation-inducing factors in serum could be equated with serum's content of $\beta$-transforming growth factor, ($\beta$-TGF). See Shipley, S. D. et al., *Cancer Res.* 46:2068–2071 (1986). It has also been reported that normal human keratinocytes actually produce their own growth factors. That is, proliferating basal cells are stimulated to secrete $\alpha$-transforming growth factor ($\alpha$-TGF) in the presence of added epidermal growth factor (EGF) and decrease production of $\alpha$-TGF at high cell densities near confluence. Under the latter condition, the arrested cells secrete an inactive form of $\beta$-TGF. See Coffen, R. J. et al., *Nature* 328:817–820 (1987). These considerations led the inventor to the idea that the natural mechanism of growth stimulation and its regulation in cultured epithelia cells could be accomplished through manipulation of the various media components and that such manipulation would also eliminate the need for an organic substrate or organotypic matrix as well.

Judd et al. discuss a keratinocyte growth medium designated keratinocytes-SFM in an article entitled: "Culture of Human Keratinocytes in Defined Serum Free Medium", *Focus*, 19, No. 1, Pgs. 1–5. This serum-free media is also disclosed in a Gibco Product brochure. However, the actual composition of the SFM media is not disclosed other than it does not contain the growth promoting additives insulin, epidermal growth factor and fibroblast growth factor.

An article by Wille et al., in *J. Dental Research*, 68:1019 (1989) entitled "Serum Free Cultures of Normal Human Gingival Keratinocytes (HGK)" discusses the successful in vitro culturing of human gingival keratinocytes in MCDB 153 medium, supplemented with 0.1 mM ethanolamine, 0.1 mM phosphoethanolamine, 0.5 $\mu$m hydrocortisone, 5 ng per ml epidermal growth factor, 5 $\mu$g per ml insulin and 35 $\mu$g per ml bovine pituitary extract protein where the presence of these proteins is necessary, but their function is unknown in this heterogeneous tissue extract mixture.

Wille et al. in *The Journal of Cellular Physiology*, 150:52–58 (1992) in an article entitled "Effects of Growth Factors, Hormones, Bacterial Lipopolysaccharides and Lipotechoic Acids on the Clonal Growth of Urethreal Epithelial Cells in Serum Free Culture", discloses the use of F-12 media containing bovine pituitary extract and bovine serum albumin for culturing cells isolated from human ureters, again where such tissue products have necessary but unknown effective components.

Chopra et al. in the *Journal of Cellular Physiology*, 130:173–181 (1987) entitled: "Propagation of Differentiating Normal Human Tracheobronchial Epithelial in Serum Free Medium" discloses the use of a medium similar to MCDB 151 except that it contains 5.4 mg per ml HEPES, 6.1 mg per ml sodium chloride, 0.3 mg per ml sodium acetate and 1 mg per ml sodium bicarbonate. These changes lowered the final osmolarity of the disclosed medium to 290 mosmols. The concentration of HEPES in the Chopra et al. solution was 28 mM.

U.S. Pat. No. 5,328,844 to Moore discloses a culture medium useful for establishing, growing and maintaining mammalian cells in culture, in particular for the establishment of culture of human, normal and malignant cells. The claimed media contains 4,500 mg per liter of HEPES and 5 mg per liter of insulin. This patent does not relate to nor disclose media useful for growth of normal epithelial cells.

In an article by Boisseau et al. entitled "Production of Epidermal Sheets in a Serum Free Culture Medium: A Further Appraisal of the Role of Extracellular Calcium", *Journal of Dermatological Science*, 3 (1992), 111–120, the author discloses the serum-free media (MCDB 153) to grow keratinocyte monolayers in clonogenic conditions. The effect of extracellular calcium and temperature on proliferation and differentiation of cultured keratinocytes was investigated.

U.S. Pat. No. 4,673,649 to Boyce et al. discloses a basal medium which was MCDB 152 supplemented with epidermal growth factor, transferin, insulin, hydrocortisone, ethanolamine, phosphoethanolamine and progesterone to obtain a medium for growth of human keratinocytes. The inventor of the present application in U.S. Pat. No. 5,292,655 demonstrates that progesterone inhibits optimal growth.

Wilke et al. in "Biologic Mechanisms for the Regulation of Normal Human Keratinocyte Proliferation and Differentiation", *American Journal of Pathology*, Vol. 131, No. 1, April, 1988, describe a serum-free medium with low calcium concentrations on the order of 0.1 mM. These studies of Wilke et al. actually used MCDB 153 medium supplemented with insulin, EGF and protein of bovine pituitary extract where any effective components are unknown in the extract.

U.S. Pat. No. 5,232,848 to Wolfe et al. discloses a nutrient medium for both high and low density culture of a wide variety of non-epithelial cell lines and cell types. This patent discloses and claims a zwitterionic buffer such as HEPES at a concentration of $2.5 \times 10^{-2}$ moles.

Boyce et al. in U.S. Pat. No. 4,940,666 discloses and claims a growth medium which is free of transferin, comprising complete MCDB 153, EGF and insulin.

Nissley et al. in "Growth and Differentiation of Cells in a Defined Environment", pgs. 337–344 discloses that cells of embryonic and fetal origin produce IGF-1 and IGF-2 which may be important for the control of embryonic and fetal growth. The authors also suggest that the use of these cells could potentially stimulate the growth of the same or neighboring cells and thereby avoid the inclusion of such growth factors in a culture medium.

Boyce et al. in "Calcium Regulated Differentiation of Normal Human Epidermal Keratinocytes in Chemically Defined Clonal Culture and Serum Free Serial Culture", in *The Journal of Investigative Dermatology*, 81:33S–40S (1983) discloses MCDB 153 supplemented with a number of growth factors and an optimum level of calcium at 0.3 mM for colony forming efficiency and a high calcium concentration of 1.0 mM for induction of stratification and terminal differentiation.

U.S. Pat. No. 5,326,699 to Torishima et al. discloses a serum-free medium for culturing animal epithelial cells comprising 8–14 mg per ml (53.6 mM–93.8 mM) of methionine, up to 0.1 mM of calcium in the form of calcium chloride and other conventional ingredients such as glucose, growth factors, buffers and the like.

Pellegrini in "Long Term Restoration of Damaged Corneal Surfaces with Autologous Cultured Corneal Epithelium", *Lancet*, Vol. 349 (1997) discloses the culturing of corneal cells in Dulbecco, Vogt, Eagle's and Ham's F-12 Media containing fetal bovine serum, insulin, transferin, EGF and cholera toxin. The authors' report that cells isolated from the central cornea (limbus) and bulbar conjunctiva could be grown in vitro and then transplanted to the human host.

U.S. Pat. No. 4,304,866 to Green et al. discloses an in vitro method for the formation of epithelial sheets from cultured keratinocytes. The Green method uses a serum containing medium and a feeder layer of murine (mouse) fibroblast cells to accomplish cell growth and differentiation. This procedure has serious limitations for large scale production of human epithelium as the use of serum inextricably confounds the culture of purely basal cells with the dynamics of serum-induced differentiation. The net result is that subcultivation of such cultures yields low (<5%) clonal efficiencies preventing step wise large scale build up of uncommitted pluripotent basal cells as a prelude to their conversion into usable sheets of transplantable, histologically-complete, human epithelium. Moreover, the process of Green et al. does not describe the formation of a histologically complete epidermis. The Green et al. procedure forms an epidermis lacking a stratum corneum which is necessary for maximizing the utility of the tissue.

Prior art methods have achieved a complete epidermis, but only in the presence of a complete skin starter sample and serum-containing media that are combined with an organotypic substratum containing growth factors produced by companion cells as disclosed in U.S. Pat. No. 4,485,096. The use of any organotypic substrate as well as feeder or companion cell types, e.g. fibroblasts, seriously limits the resulting products safety and economic viability. See Nanchahal, J. et al. in *Lancet* II(8656):191–193, (1989).

In order to remedy these deficiencies, the inventor has dispensed with serum-containing media, eliminated any substratum support, dispensed with the requirement for innumerable skin starter samples, and designed a novel and unobvious medium capable of supporting the growth and development of a complete epithelium. Moreover, the identification of essential process steps leading to a functional epithelium has been discovered and can be monitored with specific monoclonal antibodies. The prior art media which contain undefined serum and/or feeder cell factors and/or organotypic substrates and millimolar concentrations of $Ca^{2+}$, high levels of buffers, inadequate levels of amino acids and incorrect osmolalities were not designed for the unlimited proliferation of undifferentiated basal cells. The prior art media allows cultures to spontaneously undergo maturation and uncontrolled differentiation. In contrast, the serum-free media described in this invention produces a complete epithelium.

SUMMARY OF THE INVENTION

There is disclosed an aqueous solution for isolating epithelial cells from animal tissue, said solution comprising:

a) glucose at a concentration of about 10 mM;

b) N-(2-OH-ethyl-) piperazine-N'-(2-ethanesulfonic acid) (HEPES) at a concentration of 16–22 mM;

c) sodium chloride at a concentration of 90–140 mM;

d) potassium chloride at a concentration of about 3 mM;

e) sodium orthophosphate ($Na_2HPO_4.7H_2O$) at a concentration of 1 mM;

f) phenol red at a concentration of 0.0033 mM;

g) about 100 units of penicillin per ml of solution;

h) about 100 units of streptomycin per ml of solution; and i) one component selected from the group consisting of:
   (i) trypsin at a concentration of 0.1%–0.2% w/v; and
   (ii) soy bean trypsin inhibitor at a concentration of 0.1–1.0% w/v.

The aqueous solution for the isolation of the basal epithelial cells or cell competency solution (CCS) is actually two solutions, the first being a solution containing trypsin to digest the cells of interest from other cellular tissue and the second being a solution containing a soybean trypsin inhibitor to stop the digestion of the tissue.

In a more preferred embodiment of the cell competency solution, the sodium chloride is at a concentration of 100 to 130 mM; the HEPES is at a concentration of 18 to 21 mM; the trypsin is at a concentration of 0.12 to 0.18% w/v in the digestion solution and the soybean trypsin inhibitor is at a concentration of 0.3 to 0.8% w/v in the second CCS.

The present invention also relates to a method for the isolation of basal epithelial cells from animal tissues, said method comprising the steps of:

a) obtaining animal epithelium;

b) comminuting said epithelium;

c) placing said comminuted epithelium in the cell competency solution described above containing trypsin at a temperature and for a time sufficient to allow separation of the basal epithelial cells from the epithelium;

d) collecting said epithelial cells; and e) passaging said basal epithelial cells to the CCS containing soybean trypsin inhibitor.

It should be understood that the method described above uses two (2) CCS solutions: (1) a solution containing trypsin to digest the tissue; and (2) a solution containing a soy bean trypsin inhibitor to terminate the digestion of the tissue.

In its broadest sense, the present invention relates to the use of a serum-free medium for culturing animal epithelial cells comprising:

a) N-(2-OH-ethyl-) piperazine-N'-(2-ethane-sulfonic acid) at a concentration of 14–22 mM;

b) sodium chloride at a concentration of 100–120 mM;

c) histidine at a concentration of 0.1–0.25 mM;

d) isoleucine at a concentration of 0.05–0.5 mM;

e) methionine at a concentration of 0.1–0.5 mM;

f) phenylalanine at a concentration of 0.1–0.5 mM;

g) tryptophan at a concentration of 0.05–0.5 mM; and h) tyrosine at a concentration of 0.1–0.5 mM.

This serum-free medium of the invention is sometimes hereinafter referred to as the BASAL medium.

There is further disclosed a serum-free medium for culturing animal epithelial cells comprising:

a) N-(2-OH-ethyl-)piperazine-N-(2-ethane-sulfonic acid) at a concentration of 14–22 mM;

b) sodium chloride at a concentration of 100–120 mM;

c) histidine at a concentration of 0.1–0.25 mM;

d) isoleucine at a concentration of 0.05–0.5 mM;

e) methionine at a concentration of 0.1–0.5 MM;

f) phenylalanine at a concentration of 0.1–0.5 mM;

g) tryptophan at a concentration of 0.05–0.5 mM;

h) tyrosine at a concentration of 0.1–0.5 mM; and i) insulin like growth factor −1 at a concentration of 0.3–30 ng/ml.

The serum-free medium described above is sometimes referred to as HECK-109 FS.

In addition, there is disclosed a serum-free medium for culturing animal epithelial cells comprising:

a) N-(2-OH-ethyl-)piperazine-N'-(2-ethane-sulfonic acid) at a concentration of 14–22 mM;

b) sodium chloride at a concentration of 100–120 mM;

c) calcium $^{2+}$ ions at a concentration of 0.7–3.0 mM;

d) histidine at a concentration of 0.1–0.25 mM;

e) isoleucine at a concentration of 0.05–0.5 mM;

f) methionine at a concentration of 0.1–0.5 mM;

g) phenylalanine at a concentration of 0.1–0.5 mM;

h) tryptophan at a concentration of 0.05–0.5 mM;

i) tyrosine at a concentration of 0.1–0.5 mM; and j) beta-transforming growth factor at a concentration of 3.0–30 ng/ml.

This inventive serum-free medium is sometimes hereinafter referred to as HECK-109 DM.

There is further disclosed a serum-free medium for culturing animal epithelial cells comprising:

a) N-(2-OH-ethyl-)piperazine-N'-(2-ethane-sulfonic acid) at a concentration of 14–22 mM;

b) sodium chloride at a concentration of 100–120 mM;

c) calcium $^{2+}$ ions at a concentration of 0.7–3.0 mM;

d) histidine at a concentration of 0.1–0.25 mM;

e) isoleucine at a concentration of 0.05–0.5 mM;

f) methionine at a concentration of 0.1–0.5 mM;

g) phenylalanine at a concentration of 0.1–0.5 mM;

h) tryptophan at a concentration of 0.05–0.5 mM;

i) tyrosine at a concentration of 0.1–0.5 mM; and j) linoleic acid at a concentration of 1–15 µg/ml.

The above described serum-free medium according to the invention is sometimes hereinafter referred to as HECK-109 CM.

The present invention also relates to a method for the formation of a histologically complete, stratified animal epithelium using the media described herein. More specifically, there is disclosed a method for the formation of a histologically complete, stratified human epithelium comprising the steps of:

a) isolation of basal stem cells from animal epithelium using the CCS that contains trypsin;

b) recovering said basal stem cells using CCS that contains soy bean trypsin inhibitor;

c) culturing said isolated basal stem cells in HECK-109 FS medium to form a confluent sheet of undifferentiated epithelial tissue;

d) culturing said sheet of undifferentiated epithelial tissue in HECK-109 DM to form a sheet of differentiated and stratified tissue; and e) culturing said differentiated and stratified tissue in HECK-109 CM to form a cornified epithelium.

In a preferred embodiment, the method of the present invention forms a histologically complete human skin.

The invention further relates to the formation of a differentiated and stratified tissue wherein the method is set forth above with the omission of step e) wherein the cornified epithelium layer is formed. The inventive method wherein cornification is omitted is preferably applied to tissue such as cornea and gingiva.

DETAILED DESCRIPTION OF THE INVENTION

The epithelial cells that can be advantageously cultured with the media of this invention include adult epidermal keratinocytes, adult corneal epithelial cells, ureteral epithelial cells, gingival keratinocytes, fetal epithelial cells and the like. As discussed in the Background section, the cell culture media according to the invention are beneficial in growing any epithelium such as the cornea of the eye and linings of the respiratory, digestive and genitourinary tissues.

The present invention also relates to a method of culturing animal epithelia comprising culturing said cells in the serum-free media disclosed above.

The important aspects of the inventive media include the low levels of HEPES, modified levels of amino acids and a particular range of osmolalities. The acceptable osmolarities of the media of this invention can range from 275 to 310 milliosmols per liter of solution (mosmols). Osmolarity is the concentration of an osmotic solution when measured in osmols or milliosmols per liter of solution. The inventor has also found that the reduced levels of HEPES, the sodium chloride concentration, (which is directly related to osmolarity) and the concentration of the six (6) amino acids, allows for the omission of serum and any foreign protein factor in the medium and is the basis for the basal medium hereinafter designated HECK-109. Further, an additional point of novelty resides in the use of insulin like –1 growth factor at a concentration of 0.3–30 ng/ml for the fully supplemented growth medium hereinafter designed HECK-109 FS. Additional points of novelty relate to the calcium $^{2+}$ ion concentration of 0.7–3.0 mM and the inclusion of β-transforming growth factor at a concentration of 3.0–30 ng/ml for the differentiation medium hereinafter designated HECK-109 DM. An additional inventive media comprises linoleic acid at a concentration of 1–15 μg per ml for cornification of the reformed tissue hereinafter designated HECK-109 CM.

Admittedly, the prior art is replete with numerous cell culture media. For example, the previously discussed Wolfe, Boyce, Wilke and MCDB media are well known and commercially available. However, none of these references have suggested or disclosed the improvements the inventor has discovered herein. Those improvements relate to the reduced level of HEPES in combination with the specific and specified levels of six very critical amino acids. Further, while many of the references recite that they are serum-free, they are in fact not tissue-extract free as the various prior art media are taught to utilize various tissue extracts such as bovine pituitary extract.

Most of the major nutrients and other factors essential for cell growth are known and have been used previously and in many permutations. However, the concentrations of certain specific components have been newly formulated for the media of this invention. The components have not merely been optimized but rather a significant discovery has been made in that the components of HEPES and the amino acids are an interrelated set of factors and enhancers for the growth of human epithelial cells. The inventor herein has also discovered that this interrelationship of the various components can also avoid the use of feeder layers such as mouse cells, which are used to produce serum-like growth factors. The novel media of the invention also allows for the avoidance of bovine pituitary extract as taught and suggested by the prior art. As will be demonstrated below, these changes to the media have a profound effect on the media's ability to allow for prolific cell growth and the ultimate differentiation of the cells into a complete epithelium.

An additional aspect of the present invention resides in the discovery that the prior art levels of the aromatic amino acids (histidine, phenylalanine, tryptophan and tyrosine) presented the cultured cells with a rate limiting amount of these vital nutrients. As such, the present inventor has included in his media significantly different amounts of each of these amino acids. Also critically important is the ratio of the amino acids to each other as the ratios impart the ability of this medium to allow the cultured cells to thrive and form a confluent sheet of tissue without the need for serum components or components derived from serum.

Thus, there is disclosed the formulation and use of novel mediums which have been differently supplemented to provide for the achievement of cellular differentiation of pluripotent basal epithelium cells to a fully differentiated human epithelium in vitro. The various media have been designated: (i) CCS for cell competency solution; (ii) HECK-109, the basal medium for cell starting; (iii) HECK-109 FS (fully-supplemented) medium for control over cellular growth; (iv) HECK-109 DM (differentiation medium) for the induction of differentiation; and (v) HECK-109 CM (cornification medium) designed for the induction of cellular differentiation to form a cornification layer. The invention also relates to a sequential process for the in vitro construction of a histologically-complete living epithelium in a totally serum-free medium. The process and media of the invention does not require feeder layer cells and is also matrix-free (i.e., collagen or other organotypic matrix).

The nutrient basal medium designated HECK-109 has as critical components: (i) N-(2-OH-ethyl-)piperazine-N'-(2-ethane sulfonic acid) (hereinafter "HEPES") at 14–22 mM; ii) NaCl at 100–120 mM; and (iii) six (6) key amino acids at about the following concentrations: histidine at $1.0–2.5\times10^{-4}$ M; isoleucine at $0.5–5.0\times10^{-4}$ M; methionine at $1.0–5.0\times10^{-4}$ M; phenylalanine at $1.0–5.0\times10^{-4}$ M; tryptophan at $0.5–5.0\times10^{-4}$ M; and tyrosine at $1.0–5.0\times10^{-4}$ M. Taken together, HEPES, NaCl and the six (6) key amino acids are superior to any previous media or similar design, in toxicity, osmolarity and support of clonal growth of basal epithelial cells. All media of this invention, except for the CCS, have an osmolarity of between 275 to 310 mosmols.

The second media is a growth medium for undifferentiated basal epithelial cells and is based on HECK-109 basal medium and herein designated HECK-109 FS. HECK-109 FS consists of HECK-109 supplemented with insulin-like growth factor-1 (IGF-1) at 0.3–30 ng/ml. This medium is selective for the growth of normal human epithelial cells and is essential for Phase I of the culture growth in that it supports the formation of a hole-free monolayer (intack sheet) of undifferentiated epithelial cells while suppressing growth-arrest and any significant decline in clonogenic potential. These properties are unlike any previous media used to support proliferation for basal epithelial cells.

The third medium is HECK-109 DM and is a differentiating growth medium based on HECK-109 FS with the addition of beta-transforming growth factor at a concentration of 3.0 to 30 ng/ml. As detailed in Example 4, the induction of synchronous growth arrest, commitment to terminal epithelial differentiation and formation of a suprabasal cell layer superimposed on top of a proliferation-competent basal cell layer is achieved by replacement of HECK-109 FS with HECK-109 DM. HECK-109 DM is also HECK-109 FS with $Ca^{2+}$ at a concentration of about 0.7 to 3.0 mM. Addition of β-TGF is required to arrest basal epithelial cells through a pathway that prepares the monolayer for induction of stratification, a step under the joint control of EGF (1–5 ng/ml), β-TGF (3–30 ng/ml) and $Ca^{2+}$ (0.6–3.0 mM).

HECK-109 DM is replaced by HECK-109 CM (cornification-inducing medium) when a cornified layer is required in the epithelium. HECK-109 CM is based on HECK-109 FS minus the protein factors and with the addition of linoleic acid at 1–15 μg/ml and $Ca^{2+}$ ions at 0.7–3.0 mM.

The present invention also relates to a method using CCS wherein clonally competent basal epithelial cells are isolated from human epithelium by the procedures set forth in Example 1. The inventive method and CCS allows for the recovery of a unique subpopulation of basal cells which differs from basal cells obtained using other techniques and media. Separation of these unique basal cells from the starting epithelium is accomplished by digestion in CCS containing 0.1–0.2% trypsin (w/v). CCS is designed to permit the initial isolation of a subpopulation of clonally competent basal epithelial cells that retain a high level clonality. This is due to the low toxicity of the CCS with improved osmolarity. CCS according to this invention differs from all other isolation solutions for such cells. The approximate composition of CCS is as follows: glucose at about 10 mM; KCl at about 3 mM; NaCl at 100–120 mM; $Na_2HPO_4.7H_2O$ at about 1 mM; phenol red at about 0.0033 mM; HEPES at 16–22 mM; about 100 units both of penicillin and streptomycin and SOTI at 0.2–2.0% (w/v) or trypsin at 0.1–0.2% w/v. It should be noted that CCS containing trypsin is used to digest the epithelium and the released basal cells are harvested in the CCS containing SOTI. The isolated competent basal cells are then seeded into HECK-109 FS at about $1-5 \times 10^3$ cells/cm$^2$ and are amplified to a density of $2 \times 10^4$ to $1 \times 10^5$ cells/cm$^2$ prior to serial passaging.

For large scale preparation of tissue, the undifferentiated basal cells are amplified by serial propagation in HECK-109 FS until a sufficient quantity of tissue has been obtained. This is known as Phase I. In the next step, the cells are differentiated by replacement of HECK-109 FS with HECK-109 DM, at this time the culture has attained a confluent cell density ($1-2 \times 10^5$ cells/cm$^2$). This step is known as Phase II. The cells are cultured under HECK-109 DM for about 1 week, during which time the cells complete their commitment to differentiation, stratification and keratinization.

Finally, in those cases where a cornified layer is required in the epithelium, the HECK-109 DM is replaced by HECK-109 CM. This is known as Phase III.

The present invention also discloses a process wherein a viable, and completely reformed human epithelium can be grown in culture by following a sequence of steps heretofore unknown using cell culture media that do not contain serum, feeder cells or organotypic substrates. The starting material (tissue) can be obtained from fetal tissue, neonatal foreskins and adult epithelial and requires only about 0.1 to 2 cm$^2$. More preferably, the starting material should be at least 1–2 cm$^2$. Representative of other epithelial cells that can be used in this invention are those tissues obtained from cornea, ureter and gingiva. In fact, any epithelium of an animal body can be used to obtain the basal cells which are then cultivated and differentiated using the process and media of this invention.

Phase I typically amplifies the initial input of basal cells by a factor of 100,000. Typically, this requires less than two weeks and provides enough basal cells to eventually form about 2 to 3 square meters of viable cultured epithelium.

The reformed epithelium produced in accordance with the invention consists of at least two cellular layers. Representative is the epidermis which consists of three histologically recognizable and antibody-identifiable cell layers, a bottom-most cell layer (stratum germinativum), a spinous cell layer (stratum spinosum) above it, and a top-most granular cell layer (stratum granulosum), but no formation of a cornified stratus (stratum corneum), or bordering layers, (e.g., statum lucidum and stratum disjunction). This development requires a third phase of culture. The second phase culture, characterized by an incomplete epidermis, will persist in culture for an extended period (>30 days). It will, however, lose the capacity to convert to a complete epidermis which is prevented by replacement of HECK-109 DM with HECK-109 CM.

The present invention produces a completely differentiated human epithelium in a manner that is vastly superior to any prior art method employing serum-containing media and/or feeder layer support and/or organotypic matrices. The present invention also affords the possibility of intervening at any of the crucial steps in the process that allows one to augment the cellular content of one of the living versus nonliving cell layers. Finally, the ease of amplifying the initial input through rapid serial cell culture makes this the choice method for instituting autografts for severe bum patients. The present invention also provides a long term solution to patients in need of a corneal transplant, gingiva repair, ureter reconstruction and the like.

The following Examples are intended to be illustrative and not limitative. Values presented in parenthesis are an acceptable range for the given element, unless stated otherwise.

EXAMPLE 1

Primary and Secondary Culture of Normal Human Epidermal Keratinocytes in HECK-109 Serum-Free Medium Isolation of Basal Cells and Primary Cultures Primary cultures of normal human basal epidermal keratinocytes were started by subjecting full-thickness skin samples to enzymatic digestion. Skin obtained from biopsies or autopsies was first cleaned of adhering subdermal fat and the dermis was reduced to less than 3 mm in thickness. The skin sample was then cut into 8 to 12 small pieces (usually 0.5 cm$^2$). These pieces were floated on top of sterile CCS (Cell Competency Solution). CCS consisted of glucose, 10 mM; KCl, 3 mM; NaCl, 130 mM; $Na_2HPO_4$, $7H_2O$, 1 mM; phenol red, 3.3 μM; HEPES at 23 mM; (See Shipley, G. D. and Ham, R. G., In Vitro 17:656–670 (1981)) and 0.17% trypsin (w/v) and 100 units/ml of both penicillin and streptomycin. After 14 to 16 hours of digestion at 4° C., the dermis was separated from the epidermis by a split-dermis technique. This was accomplished by placing the cornified side of the epidermis on a clean sterile polystyrene surface whereupon the epidermis spontaneously detaches, and the dermis is removed with sterile forceps. Trypsin digestion cleaves the skin along a fracture line which separates some of the basal cells with the dermis, but frees other basal cells lying between the dermis and the fracture line just above the basal cell layer.

The trypsin-treated epidermis, so split from the dermis, was enriched for a subpopulation of loosely-associated, clonally competent basal cells. In a series of experiments, the inventor herein discovered that these loosely-associated basal cells are larger than the basal cells that remain associated with the dermis. Moreover, these larger basal cells are separable by cell sorting procedures using a fluorescence-activated cell sorting device. They also have a greater colony-forming ability than the dermis-associated basal cells, as demonstrated by tonal growth experimentation.

The loosely-associated basal cells were collected in ice-cold (0–4° C.) CCS containing 0.1–1.0% w/v SOTI solution in place of the trypsin. The cell suspension was then filtered on ice through a 100 micrometer sized Nylon mesh using sterile procedures. Filtration removes the cell aggregates and ensures preparation of a single cell suspension. The cells were pelleted by low speed centrifugation (800×g (gravity), 5 mins.) at 4° C. The CCS containing SOTI was aspirated off and the remaining cells were resuspended by gentle pipetting in CCS, and washed once with ice-cold HECK-109 (serum-free basal nutrient medium; see Example 2 for detailed preparation of this medium). The centrifugation step was repeated as above, and the resulting cell pellet was resuspended in 1 to 2 ml of HECK-109. Cell counts were obtained by standard cell chamber counting methods. Primary cultures were initiated into HECK-109 FS supplemented with 0.1 (0.05–0.20) mM ethanolamine; 0.1 (0.5–0.20) mM phosphoethanolamine; 0.5 (0.1–1.0) $\mu$M hydrocortisone; and 5 ng/ml EGF. Antibiotics which were added at this time can be removed 2 to 3 days later when the proliferating cell cultures are refed fresh HECK-109 FS. The two protein growth factors (EGF and IGF-1) were added aseptically to the medium. All media was sterilized through a commercially available membrane filter (0.2 microns). The initial seeding density for initiating the primary culture is $5 \times 10^3$ basal cells per $cm^2$ tissue culture flask. Two flasks were set up from an initial yield of 1 to $2 \times 10^6$ cells isolated from the 2 $cm^2$ piece of skin. It should be appreciated that the same isolation procedure used for basal keratinocytes from skin can be used to obtain other basal epithelia cells from tissues such as cornea, gingiva, ureter and the like.

Secondary Culture Procedure—Secondary cultures may be initiated from either primary cultures or early passage secondary cultures. Early passage secondary cultures were passaged by enzymatic dissociation of cells. This serial passage technique is not standard. It involves the use of ice-cold 0.02% (0.02–0.20) SOTI (w/v) in CCS as detailed above for initiating primary cultures. Secondary cultures were seeded at an initial cell density of 1000 cells per $cm^2$. Lower seeding densities are also acceptable.

The procedure for calculating colony forming efficiency (CFE) of the basal cells recovered from the epidermis and used to initiate a primary culture is based upon setting up duplicate primary cultures at 5000 cells per $cm^2$ as described above, and then to count the number of cells which attach and later form a colony of at least 8 or more cells, three days after seeding the primary culture. By this method, the percent attachment of epidermal cells was 50 to 60 percent of the input cells.

EXAMPLE 2

Preparation of HECK-109 Basal Nutrient Medium

One aspect of the present invention relates to the preparation of a new media suitable for the large scale amplification of both primary and secondary cultures of normal human epithelial cells, such as keratinocytes, and for conversion of proliferating normal human epithelial monolayer cultures to a fully differentiated tissue transplantable to a human being. More particularly, this Example 2 is directed to the materials and procedures for preparation of a basal nutrient medium (Human Epidermal Cell Keratinocyte, HECK-109), and experiments evidencing its superiority in stimulating epithelial cell growth. The media according to this invention are novel and unobvious by design of the osmolarity, toxicity and pH-buffering properties.

Table I below details the concentration of components in basal medium, HECK-109. All biochemicals, growth factors and hormones were purchased from Sigma Chemical Company (St. Louis, Mo., U.S.A.), and all inorganic chemicals were from Fisher Scientific (Pittsburgh, Pa., U.S.A.). All trace elements in Stock T were from Aesor (Johnson Matthey, Inc., Seabrook, N.H., U.S.A., Purotronic Grade). EGF was prepared according to the procedure of Savage, R. C. and Cohen, S. (*J. Biol. Chem.* 247:7609–7611 (1972)), or purchased from Collaborative Research, Inc., Waltham, Mass.

One liter of HECK-109 was prepared in a separate stock solution fashion as described in Table 1 with respect to Stocks 2 through 10. Medium HECK-109 differs from all other media in the part art by its Stock 1 amino acids, its concentration of NaCl (113 mM; Range 90–140) and HEPES (20 mM; Range 14–22). The concentration of the six (6) amino acids is critical and must be within the following ranges: isoleucine at $0.5$–$5.0 \times 10^{-4}$M; histidine at $0.5$–$2.5 \times 10^{-4}$ M; methionine at $1.0$–$5.0 \times 10^{-4}$ M; phenylalanine at $1.0$–$5.0 \times 10^{-4}$ M; tryptophan at $0.5$–$5.0 \times 10^{-4}$ M; tyrosine at $1.0$–$5.0 \times 10^{-4}$ M.

TABLE 1

Composition of Basal Nutrient Medium HECK-109

| | | Concentration in Final Medium | |
|---|---|---|---|
| Stock | Component | mg/l | mol/l* |
| 1 | Arginine.HCl | 421.4 | $2.00 \times 10^{-3}$ |
| | Histidine.HCl.H$_2$O | 36.1 | $1.70 \times 10^{-4}$ |
| | Isoleucine allo-free | 33.0 | $1.50 \times 10^{-4}$ |
| | Leucine | 132.0 | $1.00 \times 10^{-3}$ |
| | Lysine.HCl | 36.6 | $2.00 \times 10^{-4}$ |
| | Methionine | 45.0 | $3.0 \times 10^{-4}$ |
| | Phenylalanine | 50.0 | $3.0 \times 10^{-4}$ |
| | Threonine | 23.8 | $2.00 \times 10^{-4}$ |
| | Tryptophan | 40.8 | $2.00 \times 10^{-4}$ |
| | Tyrosine | 54.0 | $3.0 \times 10^{-4}$ |
| | Valine | 70.2 | $6.00 \times 10^{-4}$ |
| | Choline Chloride | 27.9 | $2.00 \times 10^{-4}$ |
| | Serine | 126.1 | $1.20 \times 10^{-3}$ |
| 2 | Biotin | 0.0146 | $6.00 \times 10^{-8}$ |
| | Calcium Pantothenate | 0.285 | $1.00 \times 10^{-6}$ |
| | Niacinamide | 0.03363 | $3.00 \times 10^{-7}$ |
| | Pyridoxal.HCl | 0.06171 | $3.00 \times 10^{-7}$ |
| | Thiamine.HCl | 0.3373 | $1.00 \times 10^{-6}$ |
| | Potassium Chloride | 111.83 | $1.50 \times 10^{-3}$ |
| 3 | Folic Acid | 0.79 | $1.80 \times 10^{-6}$ |
| | Na$_2$HPO$_4$.7H$_2$O | 536.2 | $2.00 \times 10^{-3}$ |
| 4a | Calcium chloride.2H$_2$O | 14.7 | $1.00 \times 10^{-4}$ |
| 4b | Magnesium chloride.6H$_2$O | 122.0 | $6.00 \times 10^{-4}$ |
| 4c | Ferrous sulfate.7H$_2$O | 1.39 | $5.00 \times 10^{-6}$ |
| 5 | Phenol red | 1.242 | $3.30 \times 10^{-6}$ |
| 6a | Glutamine | 877.2 | $6.00 \times 10^{-3}$ |
| 6b | Sodium pyruvate | 55.0 | $5.00 \times 10^{-4}$ |
| 6c | Riboflavin | 0.03764 | $1.00 \times 10^{-7}$ |
| 7 | Cysteine.HCl | 42.04 | $2.40 \times 10^{-4}$ |
| 8 | Asparagine | 13.2 | $1.00 \times 10^{-4}$ |
| | Proline | 34.53 | $3.0 \times 10^{-4}$ |
| | Putrescine | 0.1611 | $1.00 \times 10^{-6}$ |
| | Vitamin B$_{12}$ | 0.407 | $3.00 \times 10^{-7}$ |
| 9 | Alanine | 8.91 | $1.00 \times 10^{-4}$ |
| | Aspartic Acid | 3.99 | $3.00 \times 10^{-5}$ |
| | Glutamic Acid | 14.71 | $1.00 \times 10^{-4}$ |

TABLE 1-continued

Composition of Basal Nutrient Medium HECK-109

| Stock | Component | Concentration in Final Medium | |
|---|---|---|---|
| | | mg/l | mol/l* |
| | Glycine | 7.51 | $1.00 \times 10^{-4}$ |
| 10 | Adenine | 12.16 | $9.00 \times 10^{-5}$ |
| | Inositol | 18.02 | $1.00 \times 10^{-4}$ |
| | Lipoic Acid | 0.2063 | $1.00 \times 10^{-6}$ |
| | Thymidine | 0.7266 | $2.00 \times 10^{-6}$ |
| Trace Element T | Copper sulfate | 0.0025 | $1.00 \times 10^{-8}$ |
| | Selenic Acid | 0.00687 | $3.00 \times 10^{-8}$ |
| | Manganese Sulfate.5H$_2$O | 0.000241 | $1.00 \times 10^{-9}$ |
| | Sodium Silicate.9H$_2$O | 0.001421 | $1.00 \times 10^{-7}$ |
| | Ammonium Molybdate.4H$_2$O | 0.00124 | $1.00 \times 10^{-9}$ |
| | Ammonium Vanadate | 0.00059 | $1.00 \times 10^{-9}$ |
| | Nickel Chloride.6H$_2$O | 0.00012 | $5.00 \times 10^{-9}$ |
| | Stannous Chloride | 0.000113 | $5.00 \times 10^{-10}$ |
| | Zinc Chloride.7H$_2$O | 0.1438 | $5.00 \times 10^{-7}$ |
| Solids S | Glucose | 1081.0 | $6.00 \times 10^{-3}$ |
| | Sodium Acetate.3H$_2$O | 500.0 | $3.70 \times 10^{-3}$ |
| | Sodium Bicarbonate | 1176.0 | $1.40 \times 10^{-2}$ |
| | Sodium Chloride | 6600.0 | $1.13 \times 10^{-2}$ |
| | HEPES | 4700.0 | $2.00 \times 10^{-2}$ |

*All above components come together to a final volume of 1 liter of distilled and 0.22 μm-filtered water.

The concentrations of these six (6) important amino acids have been shown by the inventor to be necessary for sustained basal cell proliferation. By further experimentation, the inventor discovered that superior growth occurs when the osmolarity of the media are between 275 and 310 milliosmoles (mosmols). The osmolarity of the inventive media are critical to proper cell growth.

Through an extensive series of clonal growth experiments in which the osmolarity was held constant at 300 mosmols and the concentration of HEPES varied between 14 to 28 mM, it was also discovered that the inventive media must incorporate HEPES at between 14–22 mM, preferably between 18 and 22 mM with 22 mM being the most preferred. This is also critical to the media of this invention. Table 2 presents results of clonal growth experiments showing that the design of HECK-109 supports a higher growth rate and a higher colony forming efficiency than a standard MCDB 153 commercial medium.

A most significant aspect of the present invention is that the concentration of 14 to 22 mM concentration HEPES in HECK-109 medium results in a 2 to 3 fold higher colony forming efficiency than that previously attainable. The second significant discovery is that an osmolarity of 280–310 mosmols, most preferably 300 mosmols, of the media permits attainment of higher saturation densities at confluence of the monolayer culture. The third significant discovery is that it is necessary to provide the indicated concentrations of 6 key amino acids present in Stock 1 (typically 2 to 5 times higher concentration than that in commercially available in MCDB 153 medium). This allows human epithelial cell cultures to routinely achieve a cell density equal to or greater than 100,000 cells per cm$^2$. HECK-109 incorporates these three discoveries in such a way that the media will allow for and fully support the formation of a complete reformed human epithelium as detailed below.

TABLE 2

Effect of Osmolarity and HEPES Concentrations on the Growth Response of Normal Human Keratinocytes

| Culture Media | HEPES (mM) | NaCl (mM) | Osmolarity (mosmols) | Growth Response (Colonies/dish) | |
|---|---|---|---|---|---|
| | | | | AKH[a] | NHK[b] |
| MCDB-153 | 28 | 130 | 340 | 84 ± 12 | 275 ± 24 |
| HECK-109 | 22 | 104 | 300 | 196 ± 23 | 438 ± 35 |

[a]-Secondary cultures of adult skin normal human keratinocytes (AHK) were seeded at $2 \times 10^3$ cells/dish in MCDB 153 medium and refed HECK-109 48 hours later. Dishes were fixed for colony counts 6 days later.
[b]-Clonal growth experiments were performed on neonatal foreskin secondary normal human keratinocytes (NHK) cultures as described in Wille, J.J. et al., J Cellular Physio. 121:31–44 (1984).

An additional experiment was conducted to investigate the effect of varying HEPES levels on the clonal growth response of normal human keratinocytes cultured on complete MCDB 153 medium prepared with 104 mM NaCl and containing five (5)different HEPES concentrations at 300 mosmols. Each dish was seeded with 500 cells and allowed to grow for 12 days at 37° C. under 5% $CO_2$.

The cells were fixed for five (5) minutes with ice-cold 2.5% formaldehyde in 1XPBS (phosphate buffered saline), washed twice at room temperature with 1XPBS and stained for 15 to 30 minutes with 0.3% crystal violet solution. The dishes were then rinsed under running tap water to remove excess dye and air dried. Stained colonies were counted with an ARTEX bacterial colony counter (Model 870). The background noise of approximately ten (10) was corrected and instrument size and level settings set at 0.27 and 0, respectively.

| HEPES Concentration (mM) | Clonal Growth Response (colonies/dish) |
|---|---|
| 28 | 187 ± 6.4 |
| 25 | 179 ± 2.0 |
| 23 | 211 ± 11 |
| 20 | 243 ± 26 |
| 14 | 295 ± 16 |

These results indicate that as the HEPES concentration decreases, the clonal growth increases wherein the relationship of HEPES concentration to clonal growth can be expressed as $y = -8.56x + 111.4$.

An additional experiment compared the osmolarity of MCDB 153 at 340 mosmols and HECK-109 at 300 mosmols on the cell densities of normal human keratinocytes after three (3) days of growth. Cells were seeded into 25 cm$^2$ flasks at a cell density of $1 \times 10^3$ cells/cm$^2$ for four (4) days earlier and fed MCDB 153, then on day 0 (cell density of 6.7 cells/cm$^2 \times 10^3$), cultures were fed either HECK-109 or MCDB-153. On day 3, the cell density of the HECK-109 FS (300 mosmols) was $44 \times 10^3$ cells per cm$^2$ while the MCDB-153 (340 mosmols) was $37.2 \times 10^3$ cells/cm$^2$. This demonstrates the importance of the correct osmolarity for the proper growth of the cells.

EXAMPLE 3

Clonal Growth Studies employing Single Cell Clones in HECK-109 Medium

Human keratinocyte cultures were initiated, from either foreskin or adult female breast skin, as detailed above in Example 1, and then placed into secondary culture in complete HECK-109 FS medium. The purpose of the following experiment was to determine the colony forming ability of individual keratinocyte stem cells obtained from different skin donors and from different passage levels of the same normal human keratinocyte sample. It is stressed here that each culture was established from a single genetic source to ensure that the responses observed represent only deliberate experimental manipulations. The technique of cloning individual cells was accomplished by seeding 1000 cells from a exponentially dividing parent culture into a 100 mm² Petri dish containing prewarmed HECK-109 FS medium. Visual observations of each such single cell isolate were made and a daily record of the number of cells formed from each single-celled clone. The results of these experiments are set forth in Tables 3 and 4. The data indicate that each proliferating basal cell from a given donor culture has an exceedingly high clonogenic potential.

Typically, a clone is comprised of more than 1000 cells, indicating that the original single cell had undergone more than 10 doublings. Such clones are, by definition, basal stem cells and data on their clonal analysis is presented in Tables 3 and 4. The results in Table 3 show that 70% of single cells derived from a third passage neonatal foreskin normal human keratinocyte cultures were, in fact, keratinocyte stem cells. Adult-derived normal human keratinocyte secondary cultures also at the third passage level had a significantly reduced clonogenic potential (48%), which correlates with the slower growth rate (48 hour doubling time) of the parent culture, which, when compared with the rapid (24 hour doubling time) of the neonatal foreskin normal human keratinocyte culture, clearly shows that the proliferative potential of stem cells is determined by prior culture conditions. Table 4 presents data comparing five (5) different neonatal foreskin normal human keratinocyte cultures and shows again, the fact that a consistently high clonogenic potential is maintained in secondary cultures under prior culture conditions.

TABLE 3

Comparison of the Proliferative Potential of Individual Adult Versus Neonatal Keratinocyte Basal Cells Prior Culture Condition[a,b]

| Clone No. | Passage No. | Cell Density ($10^4$/cm²) | Average GT (hrs) | % Proliferative Clones (N) |
|---|---|---|---|---|
| Adult | 3 | 0.4 | 48 | 48(109) |
| Neonatal | 3 | 7.5 | 24 | 70(106) |

[a]-GT is defined as the average population doubling time (in hours) of the culture.
[b]-N is the number of single cell clones tested.

TABLE 4

Clonal Analysis of the Proliferative Potential of Individual Keratinocyte Basal Cells Prior Culture Condition[a,b]

| Neonatal clone No. | Passage level | Cell density ($10^4$/cm²) | Average (GT(hr)) | % Proliferative clones (N) |
|---|---|---|---|---|
| 1 | 2 | 1.87 | 24(5)[c] | 75(32) |
| 1 | 3 | 1.73 | 24(6) | 66(35) |
| 2 | 2 | 1.0 | 24(4) | 79(34) |
| 3 | 2 | 1.1 | 24(6) | 68(37) |
| 4 | 2 | 0.65 | 30(4) | 51(93) |

Mean % = 63(231)
[a]-GT is defined as the average population doubling time (in hours) of the culture.
[b]-N is the number of single cell colonies tested.
[c]-The number in parenthesis within this column indicates the age of the parent culture in days.

In summary, the combined results of 231 single cells cloned at random from secondary cultures reared in HECK-109 FS medium showed that at least 63% were keratinocyte stem cells. The results of these single cell clonal studies indicate that the novel basal medium HECK-109 supports increased clonal growth of basal cells and enhances their clonogenic potential 10 times above the reported values obtained by Green et al. in U.S. Pat. No. 4,016,036, 1980 or in the serum-free culturing process of Boyce et al., U.S. Pat. No. 4,673,649. These considerations are of utmost relevance to the present invention and a major advancement in the state of the art. Further, the present invention allows commercially usable in vitro manufactured living skin substitutes, corneal substitutes, gingival substrates and other epithelium.

EXAMPLE 4

Formation of a Complete Epidermis in the Serum-Free HECK-109 Culture Medium

The formation of a complete reformed human epidermis in serum-free HECK-109 medium was accomplished in three separate culture phases. Phase I of the culture began with the seeding of basal keratinocyte stem cells isolated using CCS into culture dishes at a cell density of approximately 1000 cells per cm² as set forth in Example 1. Typically, several million keratinocyte stem cells were prepared from a single primary culture flask, representing about a 5000-fold increase in cells over the starting stem cells recovered from the skin sample. All normal human keratinocyte cultures were fed HECK-109 FS medium as set forth in Table I. Cultures were refed HECK-109 FS every other day until the cell density was 1 to $2 \times 10^4$ cells per cm². Cultures fed HECK-109 FS every other day typically reach confluence in six (6) to ten (10) days.

Phase II, the induction of the stratum spinosum and the stratum granulosum and concomitant maintenance of the stratum germinativum, begins with the removal of the HECK-109 FS and its replacement with HECK-109 DM. The use of HECK-109 DM overcomes the complete parasynchronous growth arrest in the $G_1$ phase of the cell cycle as seen by Shipley, G. D., et al., *Cancer Res.* 46:2068–2071 (1986) and Wilke, M. et al., *Amer. J. Pathol.* 131:171–181 (1988). The addition of HECK-109 DM to confluent monolayer cultures, induced within 48–96 hours a progressive stratification of the basal cells to form a multilayered epithelium. Concomitantly, the clonogenic potential of the culture declined only to about 50%. HECK-109 DM allows a fraction of the basal cells to escape growth arrest while the remaining basal cells go on to form the non-dividing suprabasal layer. The suprabasal cells progressively enlarge into differentiated cell types representative of the spinous and granular cell layers, and migrated to the upper layers of the multilayered epidermis where they were shed into the medium. The result of this differentiation process was the formation of an extended sheet of multilayered epidermis (end of Phase II cell culture). This process takes about a week to complete and resulted in an incomplete living epidermis comprised of a basal cell layer with an overlying Malphigian cell layer (stratum germinativum+stratum spinosum).

The final step of the culture process (Phase III) converted the incomplete epidermis to a complete human epidermis by induction in the uppermost layers of a cornified cell layer (stratum lucidum, stratum corneum and stratum disjunction). This step was accomplished by removal of the HECK-109 DM and its replacement with HECK-109 CM. During Phase III of culture, granular cells continued to mature into cornified, anucleate cells which formed the topmost layer of the completed epidermis.

EXAMPLE 5

Applications of Reformed Human Epidermis as a Living Skin Substitute

From previous studies in the literature, it is widely known that human skin is a target organ for certain sex steroid hormones. In fact, skin is the next most active site after the liver for the metabolic interconversions of steroid hormones. Nevertheless, little is known about the direct effect of sex steroid hormones such as testosterone, progesterone and estrogens on the growth and differentiation of normal human keratinocytes.

A. Effect of Sex Steroid Hormones on Basal Epidermal Cells Cultures in Serum-Free Medium.

It has been reported (Peehl, D. M. and Ham, R. G. *In Vitro* 16:516–525 (1980)) that 17-β-estradiol stimulated the growth of epidermal cells in culture. However, the stimulatory effect that was observed was minimal and occurred under less than optimal clonal growth conditions. It is believed that the medium employed by Peehl et al. and the growth factors present in that medium limited the effectiveness of the 17-β-estradiol. In view of these considerations and because living skin substitutes are an ideal model for assaying the effects of sex steroid hormones, it was decided to measure the effects of sex steroid hormones in HECK-109. This experiment was conducted to investigate the effect of testosterone, progesterone, 17-β-estradiol on the clonal growth of normal human keratinocytes in HECK-109 FS. The data contained in Table 5 evidence that both estradiol ($3.4 \times 10^{-6}$ M) and progesterone ($3.7 \times 10^{-6}$ M) exert an inhibitory action on the proliferation of basal keratinocyte stem cells derived from either newborn foreskin or adult breast skin. In contrast, testosterone ($3.7 \times 10^{-6}$ M) had only a negligible effect on the clonal growth of these cells. Further, the results show that female-derived keratinocytes are less sensitive to the inhibitory effect of the female sex steroid hormones than are the male-derived keratinocytes (provided that the keratinocytes derived from adult skin are also for some unknown reason less sensitive than newborn). The keratinocyte proliferation may be profoundly perturbed by continuous exposure to progesterone or progesterone-related steroids and therefore, these effects may need to be taken into account where reformed human epidermis is used as a model for the transdermal delivery of contraceptive steroids.

TABLE 5

Effect of Estradiol, Progesterone, and Testosterone on Clonal Growth of Normal Human Basal Keratinocytes

| Culture Condition | Growth Responses[a] (colonies/dish) | |
|---|---|---|
| | AH[b] | NF[c] |
| HECK-109 FS medium | 569 | 286 |
| | 585 | 312 |
| +Testosterone | 603 | 259 |
| (1.0 μg/ml) | 583 | 264 |
| +Progesterone | 311 | 58 |
| (1.0 μg/ml) | 402 | 26 |
| +Estradiol | 426 | 83 |
| (1.0 μg/ml) | 363 | 58 |

[a]-Values represent the results of duplicate determinations.
[b]-AH, adult skin keratinocytes were seeded at a density of 1000 cells per dish; the dishes were fixed and counted 10 days later.
[c]-NF, foreskin keratinocytes were seeded at a density of 500 cells per dish; the dishes were fixed and counted 10 days later.

EXAMPLE 6

Demonstration of Specific and Saturable 17-β-Estradiol Receptors in Pre-Formed Human Epidermis Human epidermis prepared in accordance with the present invention was used as a tool to assay the affect of a wide variety of test substances, e.g., hormones, toxins, viruses and carcinogens. Of immediate interest is whether reformed human epidermis has specific and saturable sex steroid hormone binding sites.

A series of experiments were conducted to measure the binding of radiolabelled 17-β-estradiol to replicate samples of human epidermis from a single genetic source. Reformed human epidermis was produced by culturing basal keratinocytes as outlined in Example 4 in replicate 24-well cluster dishes (Coming Tissue Culture Wares, Coming, N.Y., U.S.A.) through Phase III of the culture. Several test wells were sampled at the time of the binding experiments by standard histological methods to verify that a complete epidermis had, indeed, been produced. The conditions of the binding assay were as follows: Phase III culture medium was aseptically removed and to the reformed human epidermis in each well, 0.5 ml of CCS containing 10 to 50 nmol of radiolabelled 17 β-estradiol (160 Ci/mM;0.2 μCi/ml) was added. The radiolabelled estradiol was purchased from New England Nuclear Corporation, Boston, Mass., U.S.A.. The concentration of radiolabelled estradiol was fixed at half maximal saturation to assure effective competition with unlabelled identical and analogue steroid hormones over a wide range of competitor concentrations. The sex steroid competitors tested in the competition binding assay were 17-β-estradiol and other analogues such as testosterone, estriol, levonorgestral and norethisterone. At the end of the 20 hour incubation interval (at 4° C.), the radiolabelled solutions were removed, the surface of the reformed human epidermis samples were rinsed gently with 1 ml of ice-cold CCS and 0.5 ml of Type IV collagenase (Dispase, 20 U/ml, Boehringer-Manheim, Los Angeles, Calif., U.S.A.) was added to each well to enzymatically release the intact epidermal sheet. The released reformed human epidermis from each treatment well was transferred to its respective vial and the contained radioactivity was counted in a scintillation spectrometer.

Only 17-β-estradiol was an efficient competitor for the 17-β-estradiol receptor. Estriol a close structural analog of estradiol also showed significant competition while testosterone and the progesterone analogues were not competitive. These results demonstrate that reformed human epidermis produced as intact epidermal sheets according to the present invention is a good model for biochemical assay of steroid sex hormone receptors. The results of this experiment also provide direct evidence for the functional fidelity of reformed human epidermis as a living skin substitute.

EXAMPLE 7

This experiment was conducted to compare the serum-free basal nutrient HECK-109 to a serum-free, commercially available basal nutrient media known as MCDB 153. The inventive media, HECK-109, was compared side by side with the same cells under identical conditions and media supplements. Basal nutrient HECK-109, was prepared according to Example 2 and its osmolarity was found to be 304 mosmols. The basal media MCDB 153 was prepared and had an osmolarity of 346 mosmols.

Normal human foreskin keratinocytes were prepared as described in Example 1 and in conformance with an article published by Wille et al., *Journal of Cellular Physiology*, 121:31–44 (1984). Primary cultures were harvested at about 50% confluence and were serial passaged into either serum-free MCDB 153 media or HECK-109 media. 100 cells were seeded into plastic, disposable Petri dishes containing media supplemented with ethanolamine at 0.1 mM; phosphoethanolamine at 0.1 mM; hydrocortisone at 0.1 M; and 0.1 mM calcium chloride. The media also contained 5 $\mu$g/ml insulin. Duplicate dishes were then further supplemented with either no epidermal growth factor (EGF) or 0.01, 0.1, 1.0 or 10 ng/ml of EGF. The dishes were incubated for 10 days at 37° C. with 5% $CO_2$ in a humidified incubator. The cells were then fixed and stained for macroscopic observation of colonies.

In every Petri dish that was fed HECK-109 medium, there was better clonal growth (more and larger colonies) as compared to the dishes fed MCDB 153 media. In addition, even in the media that did not contain EGF supplementation, HECK-109 colonies evidenced more and larger colonies and therefore demonstrated better clonal growth. There was an increasing growth response with increasing levels of EGF concentration up to 1 ng/ml EGF.

EXAMPLE 8

The experiment of Example 7 was repeated except that the HECK-109 media was prepared with 1× and 2× amounts of Stock 1 of the amino acids set forth in Table 1. The results of this experiment evidenced that HECK-109 supplemented with 1× and 2× of the Stock 1 amino acids resulted in better clonal growth than the commercially available MCDB 153 media.

EXAMPLE 9

Autologous Cultivated Corneal Epithelium

This experiment investigates the restoration of the human corneal surface with autologous corneal epithelial sheets generated by serial cultivation of limbal cells. Cells are cultivated from a 1 mm square biopsy sample taken from the limbus of the healthy eye of a patient with severe alkali burns. The procedure set forth in Example 1 for the isolation of the basal cells is conducted using the CCS. The formation of a complete reformed human cornea in serum-free HECK-109 media, was accomplished in three (3) separate culture phases. The process set forth in Example 4 was utilized except that the final step (Phase III) was not utilized to create a cornified cell layer. Graphs are prepared from confluent secondary cultures which are released from the plastic dish with the neutral protease Dispase II (Boehringer-Manheim, Germany) and mounted on a petrolatum gauze about 1.5 by 1.5 cm. The graphs typically contain about $2 \times 10^6$ cells and are about 1 $cm^2$. The graphs are then applied to the surgically ablated area of the eye.

The injured eye is prepared for transplant, draped in topical anesthesia with a lid block by 2% plain xylocaine. The conjunctival epithelium covering the cornea and limbus is removed with a blunt knife and scissors and a 360° peritomy extending for at least 2 mm beyond the limbus is conducted. The cultured epithelial graph is placed on the prepared eye, mounted on a petrolatum gauze, which is gently removed under a microscope immediately after grafting. A soft, therapeutic hydrophilic contact lens is then placed over the graft.

After grafting, the eye is patched tightly for three (3) days. The therapeutic contact lens is removed two (2) weeks after grafting.

The autologous cultured corneal epithelium prepared in accordance with this invention can restore the corneal surface of the patient with complete loss of the corneal-limbus epithelium. Long term follow up will show the stability of regenerated corneal epithelium and a striking improvement in the patient's comfort and visual acuity.

From the experiment, it will be shown that enough epithelium to cover the entire corneal-limbal epithelial surface can be obtained from a 1 mm square limbal biopsy sample, allowing minimal stem cell depletion from the healthy eye. This investigation will also demonstrate that autologous grafts prepared from limbal cultures in accordance with the methods and media of this invention, will generate an authentic corneal epithelium for patients.

EXAMPLE 10

Normal Human Gingival Keratinocyte Production

Gingivectomies are commonly performed on humans suffering from gingivitis. The excision of a portion of the gingiva for periodontal disease such as the inflammation of the gums, often leaves the patient with severely impaired oral hygiene. Through the use of the media and process of the present invention, patients prior to undergoing such a dental procedure, may have prepared in vitro, autologous tissue that can be used to replace the diseased tissue. Thus, in accordance with this invention, serum-free cultures of normal human gingival keratinocytes are prepared in a manner that begins with the isolation of competent basal cells through the use of a technique described in Example 1. The obtained basal cells are then serially passaged into the serum-free HECK-109 media as set forth in Example 4. The passaged cells are seeded onto plastic tissue culture dishes at $5 \times 10^4$ cells per $cm^2$ and fed fresh HECK-109 FS medium every other day. At the conclusion of the third phase, the human gingival keratinocytes will be studied by light and electron microscopy and will possess typical epithelial features such as desmosomes and perinucleartonofilaments The prepared tissue will react positively to monoclonal antibodies specific for basal layer cells of the human epidermis. Thus, through the process and media of the present invention, a parakeratotic stratified epithelial sheet can be produced in vitro by suitable culture manipulations which then will be useful for transplantation therapy or the tissues will provide a useful model for bacterial epithelial interactions and the effects of toxic substances on oral epithelium.

EXAMPLE 11

Growth of Ureteral Epithelial Cells in Serum-Free Culture

The term "urinary tract infection" describes a heterogeneous group of disorders localized to the urinary tract. Gram negative bacteria are the dominant cause of urinary tract infections. The initial pathogenic event in the urinary tract occurs on the mucosal surface and is the attachment of bacterial to the host mucosa. Attachment is followed by mucosal inflammation and shedding viable uroepithelial cells. Continued infection often results in the destruction of the ureter and a method for the autologous production of replacement tissue would be highly desirable.

Thus, in this experiment, cells are isolated from human ureters that are obtained after surgical removal. The basal cells from the normal human uroepithelium are isolated as set forth in Example 1. The formation of a complete uroepithelium is conducted in a manner similar to that set forth in Example 4. The sheet of human uroepithelium can then be used to test the effects of various pathogens on this tissue or can be used as a transplant material for damaged tissue.

Industrial Applicability

The present invention is directed to the design and formulation of the various novel HECK 109 media which provide for the differentiation of pluripotent basal epithelial cells to a fully differentiated human epithelium in vitro. HECK-109 is the basal medium for cell starting: HECK-109 FS is for control of cellular growth; HECK-109 DM is for the induction of differentiation and formation of a Malphigian layer and HECK-109 CM is designed for the induction of cellular differentiation in a pre-existing reformed tissue produced by HECK-109 DM. The invention also relates to a method of sequential control for the in vitro construction of a histologically complete living epithelium. The tissue derived from the media and methods of the invention have application in in vitro testing of pharmaceuticals and topical drugs; screening of toxicants, carcinogens, complete or incomplete tumor promoters; evaluation of infective human agents including viruses, e.g., human papilloma viruses, Herpes-simplex viruses and Epstein-Barr virus; and screening of cosmetics.

Most importantly the present invention allows for the use of autologously-derived tissue for transplantation in the treatment of bums or other trauma. Further, the present invention would allow for autologous production of corneal tissue, gingival tissue, ureter tissue and other epithelium for transplant to a patient in need thereof.

Numerous modifications and variations in the invention are expected to occur to those skilled in the art upon considerations of the foregoing descriptions. The invention should not be construed as limited to the preferred embodiments and modes of preparation described herein, since these are to be regarded as illustrative rather than restrictive.

We claim:

1. A method for the formation of differentiated and stratified cornea and gingiva tissue comprising the steps of:
   a) isolation of basal stem cells from said tissue using a solution comprising:
      i) N-(2-OH-ethyl-) piperazine-N'-(2-ethanesulfonic acid) at a concentration of 16–22 mM;
      ii) sodium chloride at a concentration of 90–140 mM; and
      iii) a protease;
   b) recovering said isolated basal stem cells using a solution comprising:
      i) N-(2-OH-ethyl-) piperazine-N'-(2-ethanesulfonic acid) at a concentration of 16–22 mM;
      ii) sodium chloride at a concentration of 90–140 mM; and
      iii) a protease inhibitor;
   c) culturing said isolated basal stem cells in a medium to form a confluent sheet of undifferentiated tissue, said medium comprising:
      i) N-(2-OH-ethyl-) piperazine-N'-(2-ethanesulfonic acid) at a concentration of 14–22 mM;
      ii) sodium chloride at a concentration of 100–120 mM;
      iii) histidine at a concentration of 0.1–0.25 mM;
      iv) isoleucine at a concentration of 0.05–0.5 mM;
      v) methionine at a concentration of 0.1–0.5 mM;
      vi) phenylalanine at a concentration of 0.1–0.5 mM;
      vii) tryptophan at a concentration of 0.05–0.5 mM;
      viii) tyrosine at a concentration of 0.1–0.5 mM; and
      ix) insulin-like growth factor –1 at a concentration of 0.3–30 ng/ml;
   d) culturing said sheet of undifferentiated tissue in a differentiation medium to form a sheet of undifferentiated and stratified tissue using a medium comprising:
      i) N-(2-OH-ethyl-) piperazine-N'-(2-ethanesulfonic acid) at a concentration of 14–22 mM;
      ii) sodium chloride at a concentration of 100–120 mM;
      iii) calcium $^{2+}$ ions at a concentration of 0.7–3.0 mM;
      iv) histidine at a concentration of 0.1–0.25 mM;
      v) isoleucine at a concentration of 0.05–0.5 mM;
      vi) methionine at a concentration of 0.1–0.5 mM;
      vii) phenylalanine at a concentration of 0.1–0.5 mM;
      viii) tryptophan at a concentration of 0.05–0.5 mM;
      ix) tyrosine at a concentration of 0.1–0.5 mM; and
      x) beta transforming growth factor at a concentration of 3.0–30 ng/ml.

2. The method according to claim 1 wherein:
   a) isolation of basal stem cells uses a solution comprising:
      i) N-(2-OH-ethyl-) piperazine-N'-(2-ethanesulfonic acid) at a concentration of 18–21 mm;
      ii) sodium chloride at a concentration of 90–110 mM; and
      iii) a protease at a concentration of 0.1%–0.15% w/v;
   b) recovering said isolated basal stem cells uses a solution comprising:
      i) N-(2-OH-ethyl-) piperazine-N'-(2-ethanesulfonic acid) at a concentration of 18–21 mM;
      ii) sodium chloride at a concentration of 100–110 mM; and
      iii) a protease inhibitor at a concentration of 0.3%–1.0% w/v;
   c) culturing said isolated basal stem cells to form a confluent sheet of undifferentiated tissue using a medium comprising:
      i) N-(2-OH-ethyl-) piperazine-N'-(2-ethanesulfonic acid) at a concentration of 15–21 mM;
      ii) sodium chloride at a concentration of 90–120 mM;
      iii) histidine at a concentration of 90–120 mM;
      iv) isoleucine at a concentration of 0.1–0.25 mM;
      v) methionine at a concentration of 0.05–0.5 mM;
      vi) phenylalanine at a concentration of 0.1–0.5 mM;
      vii) tryptophan at a concentration of 0.05–0.5 mM;
      viii) tyrosine at a concentration of 0.1–0.5 mM; and
      ix) insulin-like growth factor –1 at a concentration of 1.0–25 ng/ml;
   d) culturing said sheet of undifferentiated tissue to form a sheet of differentiated and stratified tissue uses a medium comprising:
      i) N-(2-OH-ethyl-) piperazine-N'-(2-ethanesulfonic acid) at a concentration of 15–21 mM;
      ii) sodium chloride at a concentration of 100–115 mM;
      iii) calcium $^{2+}$ ions at a concentration of 1.0–3.0 mM;
      iv) histidine at a concentration of 0.15–0.25 mM;
      v) isoleucine at a concentration of 0.1–0.5 mM;
      vi) methionine at a concentration of 0.2–0.5 mM;
      vii) phenylalanine at a concentration of 0.2–0.5 mM;
      viii) tryptophan at a concentration of 0.2–0.5 mM;
      ix) tyrosine at a concentration of 0.2–0.5 mM; and
      x) beta transforming growth factor at a concentration of 5.0–25 ng/ml.

* * * * *

UNITED STATES PATENT AND TRADEMARK OFFICE
CERTIFICATE OF CORRECTION

PATENT NO. : 5,912,175
DATED : June 15, 1999
INVENTOR(S) : Wille, Jr.

It is certified that error appears in the above-indentified patent and that said Letters Patent is hereby corrected as shown below:

Column 10, line 29, delete "bum" and insert - -burn- -.

Column 11, line 8, delete "tonal" and insert - -clonal- -.

Column 18, line 38, delete "Coming" (first occurrence) and insert - -Corning- -.

Column 21, line 36, delete "bums" and insert - -burns- -.

Signed and Sealed this

Twelfth Day of October, 1999

Attest:

Q. TODD DICKINSON

Attesting Officer

Acting Commissioner of Patents and Trademarks